US007642052B2

(12) United States Patent
Small et al.

(10) Patent No.: US 7,642,052 B2
(45) Date of Patent: *Jan. 5, 2010

(54) HEART FAILURE ASSESSMENT BASED ON ALPHA-2C ADRENERGIC RECEPTOR POLYMORPHISMS

(75) Inventors: Kersten M. Small, Fanwood, NJ (US); Stephen B. Liggett, Clarksville, MD (US)

(73) Assignee: University of Cincinnati, Cincinnati, OH (US)

(*) Notice: Subject to any disclaimer, the term of this patent is extended or adjusted under 35 U.S.C. 154(b) by 186 days.

This patent is subject to a terminal disclaimer.

(21) Appl. No.: 10/527,263

(22) PCT Filed: Sep. 9, 2003

(86) PCT No.: PCT/US03/28135

§ 371 (c)(1), (2), (4) Date: Jan. 11, 2006

(87) PCT Pub. No.: WO2004/023101

PCT Pub. Date: Mar. 18, 2004

(65) Prior Publication Data

US 2006/0292565 A1 Dec. 28, 2006

Related U.S. Application Data

(60) Provisional application No. 60/409,167, filed on Sep. 9, 2002.

(51) Int. Cl.
*C12Q 1/68* (2006.01)
*G01N 33/53* (2006.01)
*C07K 14/72* (2006.01)
*C07H 21/04* (2006.01)

(52) U.S. Cl. .......................... 435/6; 435/7.1; 536/23.5; 530/350

(58) Field of Classification Search ....................... None
See application file for complete search history.

(56) References Cited

U.S. PATENT DOCUMENTS 7,449,292 B2 * 11/2008 Liggett et al. .................. 435/6

FOREIGN PATENT DOCUMENTS

WO WO 01/11039 A2 2/2001

(Continued)

OTHER PUBLICATIONS

Small et al, Oct. 10, 2002. The New England Journal of Medicine. 347(15): 1135-1142.*

(Continued)

*Primary Examiner*—Bridget E Bunner
*Assistant Examiner*—Zachary C Howard
(74) *Attorney, Agent, or Firm*—Fenwick & West LLP

(57) ABSTRACT

Methods for cardiovascular disease assessment in an individual comprise detecting the presence or absence of a fragment encoding a polymorphic alpha-2C ($\alpha_{2C}$ DEL322-325) adrenergic receptor in a sample from an individual; and detecting the presence or absence of a fragment encoding a polymorphic beta-1 adrenergic receptor ($\beta_1$Arg389) in a sample from the individual. Methods for delaying development of cardiovascular disease in an individual, methods for delaying progression or early death associated with cardiovascular disease in an individual, methods of genetic counseling for cardiovascular disease in an individual are also provided.

8 Claims, 6 Drawing Sheets

FOREIGN PATENT DOCUMENTS

WO WO 01/79561 A2 10/2001

OTHER PUBLICATIONS

Li et al, 2006. Hypertension. 47: 1140-1146.*

Lobmeyer et al, 2007. Pharmacogenetics and Genomics. 17(4): 277-282.*

Small et al. 2000. Journal of Biological Chemistry. 275(30): 23059-23064.*

Small et al. 2001. Trends in Pharmacological Sciences. 22(9): 471-477.*

Small et al. 2002 (published Oct. 3, 2001). Methods of Enzymology. vol. 343: 459-475.*

Bengtsson, K., Polymorphism in the Betal-Adrenergic Receptor Gene and Hypertension, Circulation, Jul. 10, 2001, pp. 187-190, vol. 104, No. 2, American Heart Association, Dallas.

Supplementary Partial European Search Report, EP 03-79-4666, Jul. 7, 2006, 4 pages.

European Examination Report, EP 03794666.2, Jan. 3, 2008, 5 pages.

Iwai, C. et al., "Suppressive Effect of the Gly389 Allele of the Beta1-Adrenergic Receptor Gene on the Occurrence of Ventricular Tachycardia in Dilated Cardiomyopathy," Circ J., Aug. 2002, pp. 723-728, vol. 66.

European Examination Report, European Patent Application No. EP 03794666.2, Sep. 23, 2008, 2 pages.

* cited by examiner

HEART FAILURE ASSESSMENT BASED ON ALPHA-2C ADRENERGIC RECEPTOR POLYMORPHISMS

CROSS-REFERENCE TO RELATED APPLICATIONS

This application is the National Stage of International Application No. PCT/US2003/028135, published in English under PCT Article 21(2), filed Sep. 9, 2003, which claims priority to 60/409,167, filed Sep. 9, 2002.

GOVERNMENT INTERESTS

This invention was made, at least in part, with funds from the Federal Government, awarded through grant numbers NIH HL-52318 (SCOR in Heart Failure), ES-06096 and HG-00040. The U.S. Government therefore has certain acknowledged rights to the invention.

FIELD OF THE INVENTION

The present invention is directed toward methods for cardiovascular disease assessment in an individual. The present invention is also directed towards methods for delaying development of cardiovascular disease in an individual. The present invention is also directed towards methods for delaying progression or early death associated with cardiovascular disease in an individual. The present invention is further directed towards methods of genetic counseling for cardiovascular disease in an individual.

BACKGROUND OF THE INVENTION

Heart failure is a major cause of death and disability. Some common forms of heart failure include idiopathic dilated cardiomyopathy (etiology unknown), hypertensive cardiomyopathy (similar to idiopathic dilated but with antecedent hypertension), hypertrophic cardiomyopathy, and ischemic cardiomyopathy. Regardless of the initial cause, studies suggest that the enhanced chronic sympathetic drive, which is a consequence of the depressed cardiac output, ultimately plays a role in the development of clinically significant cardiac dysfunction and the progression of heart failure. Thus, it would be advantageous to develop methods to assess cardiovascular diseases in an individual.

SUMMARY OF THE INVENTION

Accordingly, it is an object of the invention to provide methods of cardiovascular disease assessment in an individual.

In accordance with one aspect of the invention, methods for cardiovascular disease assessment in an individual are provided. The methods comprise the steps of detecting the presence or absence of a fragment encoding a polymorphic alpha-2C ($\alpha_{2C}$DEL322-325) adrenergic receptor in a sample from an individual; and detecting the presence or absence of a fragment encoding a polymorphic beta-1 adrenergic receptor ($\beta_1$Arg389) in a sample from the individual.

In accordance with another aspect of the invention methods for delaying development of cardiovascular disease in an individual are provided. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\beta_1$Arg389) in a sample from the individual; and selecting a therapy regimen for the individual based on the presence or absence of $\alpha_{2C}$DEL322-325 and $\beta_1$Arg389. The therapy regimen delays development of cardiovascular disease in the individual.

In accordance with yet another aspect of the invention, methods for delaying progression or early death associated with cardiovascular disease in an individual are provided. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\beta_1$Arg389) in a sample from the individual; and selecting a therapy regimen for the individual based on the presence or absence of $\alpha_{2C}$DEL322-325 and $\beta_1$Arg389. Progression or early death associated with the cardiovascular disease is delayed.

In accordance with yet another aspect of the invention, methods of genetic counseling for cardiovascular disease in an individual are provided. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\oplus_1$Arg389) in a sample from the individual; and counseling the individual regarding the potential risk of developing a cardiovascular disease based on the presence or absence of $\alpha_{2C}$DEL322-325 and $\beta_1$Arg389.

Additional embodiments, objects and advantages of the invention will become more fully apparent in view of the following detailed description.

DETAILED DESCRIPTION OF THE DRAWINGS

The following detailed description will be more fully understood in view of the figures, wherein:

FIG. 1 is an illustration of the synergism of $\alpha_{2C}$Del322-325 and $\beta_1$Arg389 adrenergic receptors as risk factors for heart failure;

FIG. 2 is an illustration of multiple PCR detection of short tandem-repeat alleles from a single gel. The middle two lanes are ladders that represent all possible alleles from nine short tandem-repeat loci. Each multicolored lane represents fluorescence output from a single patient, which is scored by a computer algorithm. The red signals are molecular-size markers;

Figure 5:
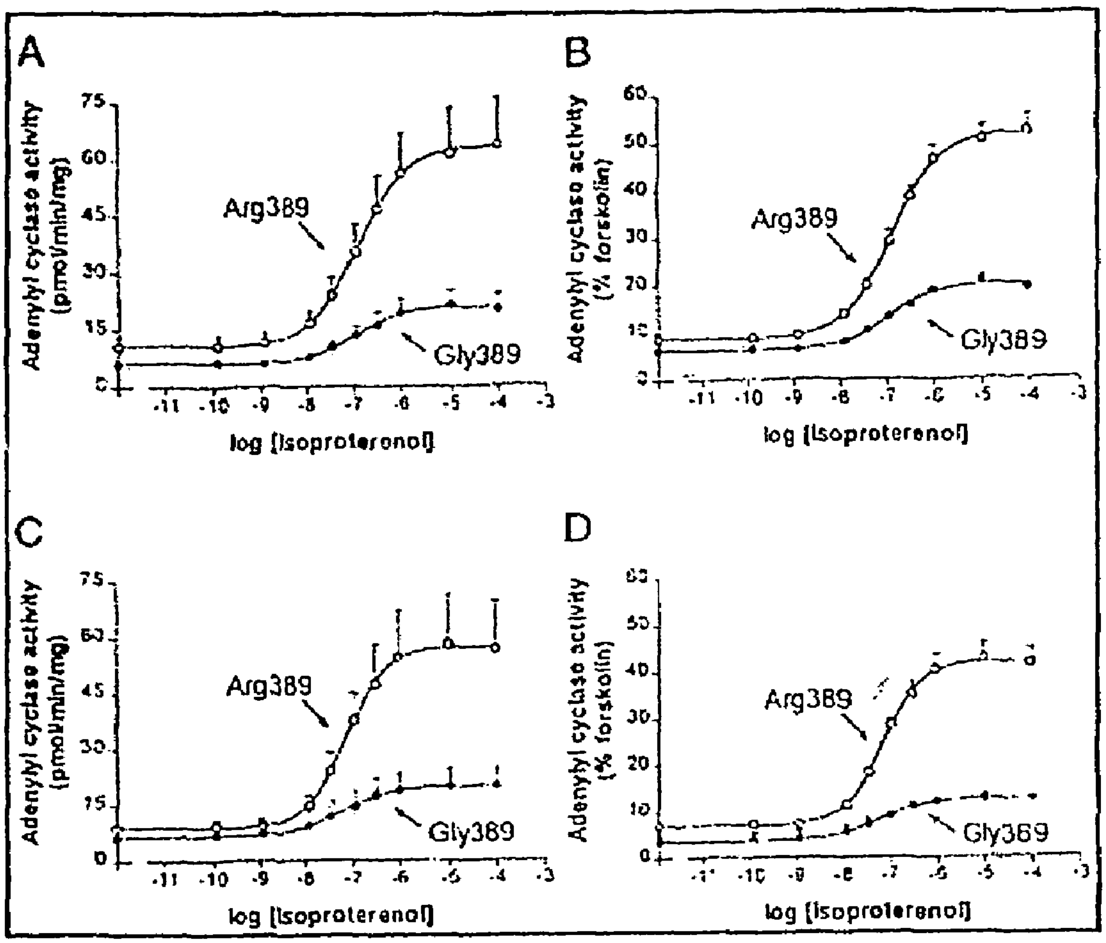
Figure 6:
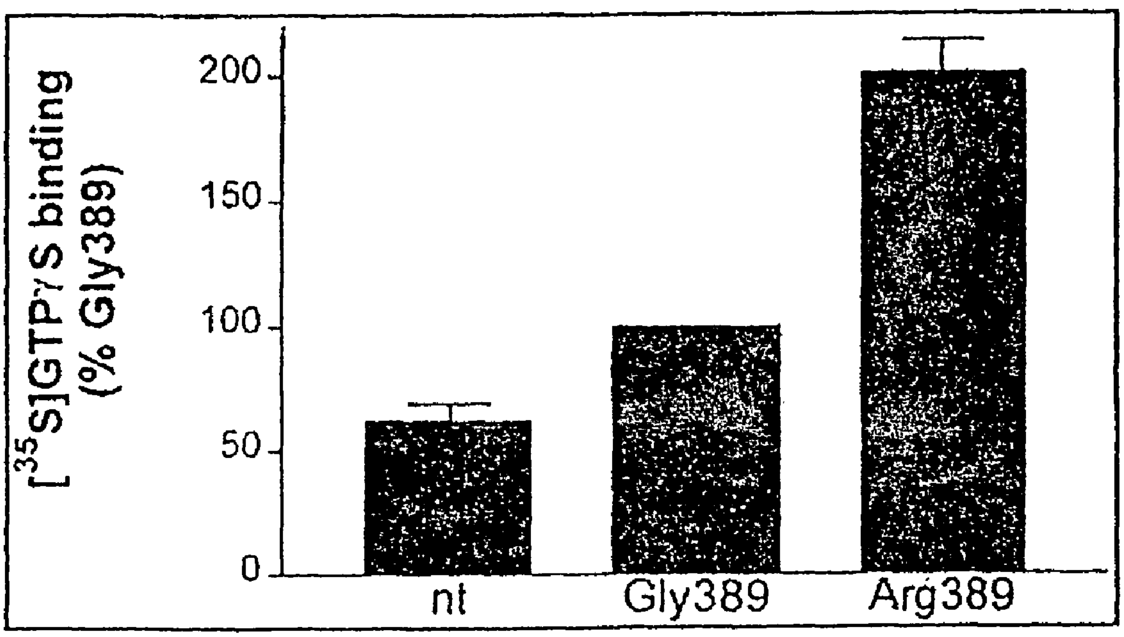

FIG. 5 illustrates functional coupling of the Gly-389 and Arg-389 receptors to adenylyl cyclase. Shown are the results from studies with clonal lines expressing each receptor at matched levels and the data presented as absolute activities (A4) and normalized to the stimulation by forskolin (B). The results of similar studies with two other clonal lines are shown in panels C and D. The Arg-389 demonstrated small increases in basal activities and marked increases in agonist-stimulated activities compared with the Gly-389 receptor. Shown are the mean results from four independent experiments carried out with each line. Absent error bars denote that standard errors were smaller than the plotting symbol; and FIG. 6 illustrates [$^{31}$S]GTPγS binding to the two polymorphic $\beta_1$ARs. Binding in the presence of 10 μM isoproterenol was greater ($p<0.05$) with the Arg-389 than with the Gly-389 receptor. Data are presented as a percentage of binding to the wild-type (Gly389) receptor (mean absolute values were $7.7\pm1.4\times10^5$ dpm/mg for Gly-389). Basal levels of binding are not different between the two receptors. nt, nontransfected cells.

DETAILED DESCRIPTION OF THE INVENTION

The major cardiac receptors which control sympathetic drive are the beta-1 adrenergic receptor ($\beta_1$AR) and the alpha-2C adrenergic receptor ($\alpha_{2C}$AR). However, there is significant interindividual variation in the expression and function of these adrenergic receptors, the development and progression of heart failure, and the response to therapy including drugs targeted to $\beta_1$AR (such as β-blockers) and $\alpha_{2C}$AR.

Chronic enhanced cardiac adrenergic stimulation has been implicated in development and/or progression of heart failure in animal models and humans. Release of norepinephrine is under negative feedback control of presynaptic alpha-2 adrenergic receptors ($\alpha_2$AR), while the target of the released norepinephrine on myocytes are beta-1 adrenergic receptors ($\beta_1$AR). The inventors have discovered that a polymorphic alpha-2C adrenergic receptor ($\alpha_{2C}$DEL322-325) displays decreased function while a polymorphic $\beta_1$AR ($\beta_1$Arg389) displays increased function. Furthermore, the inventors have discovered that the combination of these receptor polymorphisms predisposes individuals to cardiovascular disease, and in one specific embodiment, to heart failure.

Alpha-2C Adrenergic Recetor and a polymorphic form of Alpha-2C Adrenergic Receptor The alpha-2 adrenergic receptors are localized at the cell membrane and serve as receptors for endogenous catecholamine agonists i.e., epinephrine and norepinephrine, and synthetic agonists and antagonists. Upon binding of the agonist, the receptors stabilize in a conformation that favors contact with all activation of certain heterotrimeric G proteins. These include $G_{i1}$, $G_{i2}$, $G_{i3}$ and $G_0$. The $G_i$ G protein alpha subunits serve to decrease the activity of the enzyme adenylyl cyclase, which lowers the intracellular levels of cAMP (a classic second messenger). The alpha subunits, and/or the beta-gamma subunits of these G proteins also act to activate MAP kinase, open potassium channels, inhibit voltage gated calcium channels, and stimulate inositol phosphate accumulation. The physiologic consequences of the initiation of these events include inhibition of neurotransmitter release from central and peripheral noradrenergic neurons.

Specifically, the alpha-2C adrenergic receptor (alpha-2C) has been localized in brain, blood vessels, heart, lung, skeletal muscle, pancreas, kidney, prostate, ileum jejunum, spleen, adrenal gland and spinal cord. Alpha-2C plays specific roles in certain central nervous system functions. These roles include, but are not limited to, modulation of the acoustic startle reflex, prepulse inhibition, isolation induced aggression, spatial working memory, development of behavioral despair, body temperature regulation, dopamine and serotonin metabolism, presynaptic control of neurotransmitter release from cardiac sympathetic nerves and central neurons, postunctional regulation of vascular tone, or combinations thereof.

The inventors have discovered a polymorphic alpha-2C adrenergic receptor($\alpha_{2C}$DEL322-325). As used herein, the term "polymorphic" refers to a variation in the DNA and/or amino acid sequence as compared to the wild-type sequence. Often, there is a sequence of a given gene that is the most common, and this is referred to as the "wild-type", while the less common variant is referred to as the polymorphic form or the polymorphism. In some cases, the two have similar frequencies in a population and they are referred to as variants, or the specific substitution is designated in the name. Polymorphisms include, but are not limited to, single nucleotide polymorphisms (SNPs), one or more base deletions, and one or more base insertions. Polymorphisms may be synonymous or nonsynonymous. Synonymous polymorphisms when present in the coding region do not result in an amino acid change. Nonsynonymous polymorphism when present in the coding region alter one or more codons resulting in an amino acid replacement loss or insertion in the protein.

Such mutations and polymorphisms may be either heterozygous or homozygous within an individual. Homozygous individuals have identical alleles at one or more corresponding loci on homologous chromosomes. While heterozygous individuals have two different alleles at one or more corresponding loci on homologous chromosomes. Some members of a species carry a gene with one sequence (e.g., the original or wild-type "allele"), whereas other members may have an altered sequence (e.g., the variant, mutant, or polymorphic "allele").

TABLE 1

| Type | Nucleotide Position | Nucleotide | Amino Acid Position | Designation |
|---|---|---|---|---|
| Wild Type | 964-975 of SEQ ID NO: 1 | ggggcggggccg SEQ ID NO: 2 | 322-325 of SEQ ID NO: 5 | IN322-325 GAGP SEQ ID NO: 6 |
| Polymorphic | 964-975 of SEQ ID NO: 3 | ggggcggctgag SEQ ID NO: 4 | 322-325 of SEQ ID NO: 7 | DEL322-325 GAAE SEQ ID NO: 8 |

As detailed in Table 1, the wild-type alpha-2C adrenergic receptor is identified as SEQ ID NO:1 (Genbank Accession AF280399). The wild-type alpha-2C adrenergic receptor comprises ggggcggggccg at nucleotide positions 964-975 designated as SEQ ID NO:2.

SEQ ID NO: 3 (Genbank Accession AF280400) is the entire polymorphic nucleic acid sequence of alpha-2C adrenergic receptor with a deletion of SEQ ID NO:2 at nucleic acid positions 964-975. This deletion shifts the nucleotide sequence ggggcggctgag, SEQ ID NO: 4, into nucleic acid positions 964-975. Thus, SEQ ID NO: 3 comprises a twelve nucleotide deletion at nucleotide positions 964-975 when compared to the wild-type acid sequence identified as SEQ ID NO: 1.

The polymorphisms of the present invention can occur in the translated alpha-2C adrenergic receptor as well. For example, the first amino acid of the translated protein product or gene product (the methionine) is considered amino acid "1" in the wild-type alpha-2C adrenergic receptor designated amino acid SEQ ID NO: 5. The wild-type alpha-2C adrenergic receptor comprises GAGP at amino acid positions 322-325 of the alpha-2C adrenergic receptor which is designated amino acid SEQ ID NO: 6.

SEQ ID NO: 7 is the entire polymorphic amino acid sequence of alpha-2C adrenergic receptor with deletion of GAGP at amino acid positions 322-325. The polymorphic alpha-2C adrenergic receptor molecule comprises GAAE, SEQ ID NO: 8, at amino acid positions 322-325 in alpha-2C adrenergic receptor. The function of the polymorphic alpha-2C is impaired by approximately 70 percent compared to the wild-type alpha-2C adrenergic receptor.

As used herein, the entire polymorphic nucleic acid sequence of alpha-2C adrenergic receptor, as identified by SEQ ID NO: 3, may be referred to as $\alpha_{2C}$DEL964-975. Moreover, the entire polymorphic amino acid sequence of alpha-2C adrenergic receptor, as identified by SEQ ID NO: 7, may be referred to as $\alpha_{2C}$DEL322-325.

Beta-1 Adrenergic Receptor

The beta-1 adrenergic receptor ($\beta_1$AR) is a member of the adrenergic family of G-protein-coupled receptors, with epinephrine and norepinephrine being endogenous agonists. Like other members of the G-protein-coupled receptor superfamily, the amino terminus is extracellular, the protein is predicted to traverse the cell membrane seven times, and the carboxyl terminus is intracellular. In the adrenergic receptor family, agonists bind in a pocket formed by the transmembrane-spanning domains, and G-protein binding and activation occur at intracellular domains of the loops and tail, typically near the membrane.

$\beta_1$PARs couple to the slimulatory G-protein, $G_s$, activating adenylyl cyclase, as well as to non-cAMP pathways such as the activation of ion channels. $\beta_1$ARs are expressed on a number of cell types including cardiomyocytes where they serve to increase cardiac inotropy and chronotropy, adipocytes where they mediate lypolysis, and juxtaglomerular cells of the kidney where they regulate renin secretion. It has been known for decades that these responses, as well as those of the $\beta_2$AR, are somewhat variable in the human population. A common single nucleotide polymorphism resulting in a Gly to Arg switch at intracellular amino acid 389, may occur within a region important for G-protein coupling. The resulting phenotype of the Arg-389 receptor is one of enhanced receptor-$G_s$ interaction, functionally manifested as increased activation of the adenylyl cyclase effector.

In the normal human population there are two $\beta_1$ AR genetic variants with significant differences in functional signaling. The site of the variability is ~9 amino acids from the seventh transmembrane-spanning domain, in the intracellular portion of the tail prior to the proposed palmitoylated cysteine(s). This region is sometimes referred to as the fourth intracellular loop or the proximal portion of the cytoplasmic tail. By analogy with $\beta_2$AR, $\beta_2$AR, and other G-protein-coupled receptors, this region is considered important for receptor coupling to its cognate G-protein, $G_s$.

Indeed, the difference between the Arg-389 and Gly-389 receptors is in functional coupling. Receptor-promoted binding of GTPS to $G_s$, another indicator of agonist-initiated coupling to $G_s$, is similarly different between the two polymorphic $\beta_1$ARS, as illustrated in FIG. 6. Consistent with these findings, agonist-promoted accumulation of the high affinity state in washed membrane preparations in the absence of a guanine nucleotide is detected with the Arg-389 receptor but could not be resolved in studies with the Gly-389 receptor. An elevated basal activity of adenylyl cyclase (i.e. spontaneous toggling to R* in the absence of agonist) may also be expected with the Arg-389 receptor since it has a greater efficiency of stabilizing the active conformation in the presence of agonist. This functional phenotype, as shown in FIG. 5, is indicative of signaling in cells that endogenously express the two polymorphic $\beta_1$ARs.

The amino acid analogous to position 389 of the human, as well as the surrounding residues, are highly conserved in species sequenced to date, with the only deviation at position 389 being found in the human, where Gly is originally reported. The high degree of consistency in this region, its importance in G-protein coupling, and the nonconservative (size and charge) nature of the Gly to Arg substitution are consistent with this variation having functional consequences.

As introduced earlier, $\beta_1$AR are expressed on a number of cell types in the body. In the heart, $\beta_1$AR represent the predominant AR subtype and is expressed on myocytes of the atria and ventricles, where they act to increase the force and frequency of contraction in response to sympathetic stimulation. As left ventricular failure develops, $\beta_1$AR expression and function decrease in human heart failure. While not wishing to be bound by theory, the inventors believe that this response is a protective mechanism, sparing the heart from sustained sympathetic stimulation in the face of limited metabolic reserves. In earlier phases of heart disease, maintenance of $\beta_1$AR function may contribute to improved ventricular function. Given the above circumstances, the dramatic differences in function between the two $_1$AR polymorphisms suggest that the pathophysiology of congestive heart failure may be influenced by the $\beta_1$AR genotype.

The $\beta_1$AR is the predominant $\beta$AR expressed on the cardiomyocyte and is responsive to circulating epinephrine and to local norepinephrine derived from cardiac sympathetic nerves. Chronic activation of $\beta_1$AR from infusions of $\beta$-agonists in rodents results in hypertrophy, and iansgenic cardiac overexpression of $\beta_1$AR causes progressive cardiomyopathy and failure. Thus, while not wishing to be bound by theory, the inventors believe that the $\beta_1$Arg389 receptor is a risk factor, since it results in a ~200 percent increase in agonist-stimulated activity in transfected cells compared to the $\beta_1$Gly389 receptor.

Furthermore, $\beta$AR antagonists ($\beta$-blockers) are utilized in the chronic treatment of heart failure, the presumed basis of which is minimization of the aforementioned consequences of long term sympathetic stimulation. In addition, $\beta$AR agonists are used to acutely increase cardiac output during life-threatening failure. However, there is significant interindividual variation in the clinical response to $\beta$-blockers and $\beta$AR agonists in patients with heart failure. While not wishing to be bound by theory, the inventors believe that individuals bearing the Arg-389 receptor are most responsive to $\beta$-blocker and $\beta$AR agonists therapy because they would have a genetically determined $\beta_1$AR that achieves a greater stimulation of adenylyl cyclase that has enhanced function.

The Gly-389 beta-1 adrenergic receptor nucleic acid sequence is identified as SEQ ID NO: 9 (Genbank Accession J03019). The Gly-389 beta-1 adrenergic receptor amino acid sequence, identified as SEQ ID NO: 10, may be referred to as Gly-389 or $\beta_1$Gly389. The Arg-389 beta-1 adrenergic receptor nucleic acid sequence is identified as SEQ ID NO: 11. The Arg-389 beta-1 adrenergic receptor amino acid sequence, identified as SEQ ID NO: 12, may be referred to as Arg-389 or $\beta_1$Arg389.

Polymorphic Alpha-2C and Beta-1 Adrenergic Receptor

The inventors have discovered that polymorphic alpha-2C adrenergic receptors are a risk factor for heart failure. In addition, the inventors have discovered that polymorphic alpha-2C and $\beta_1$Arg389 receptors act synergistically as a risk factor for development of a cardiovascular disease in an individual. Furthermore, the inventors have determined that genotyping at these two loci may be a useful approach for identifying individuals for early or preventative pharmacologic intervention.

Figure 1:
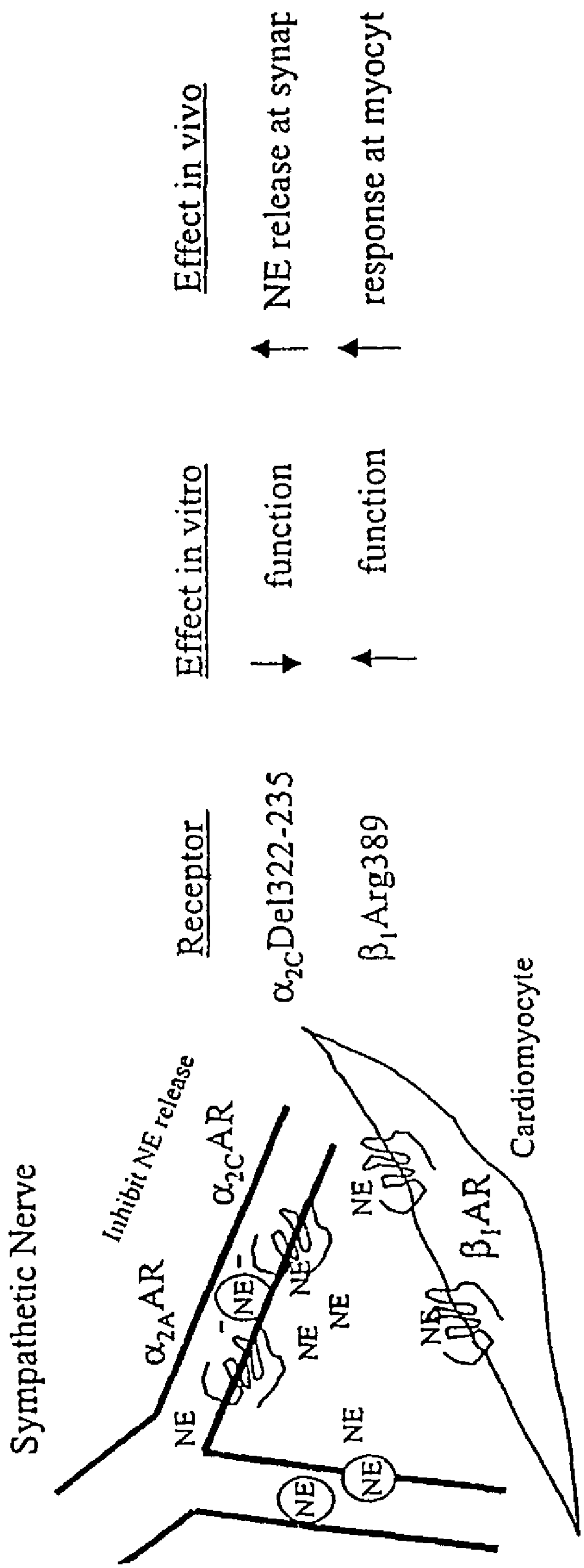

The inventors have discovered that functional polymorphisms of selected adrenergic receptors are important factors in interindividual variation, as summarized in FIG. 1. Prejunctional $\alpha_2$AR ($\alpha_2$A- and $\alpha_{2C}$AR subtypes) regulate norepinephrine release from cardiac sympathetic nerves. A polymorphic alpha-2C adrenergic receptor results in a significant loss of agonist-mediated receptor function in transfected cells A loss of normal synaptic auto-inhibitory feedback due to this dysfunction results in enhanced presynaptic norepinephrine release. Based upon this loss, the inventors have discovered that individuals with a polymorphic alpha-2C may be at risk for development of a cardiovascular disease.

Furthermore, released norepinephrine from cardiac sympathetic nerves activates myocyte $\beta_1$AR, which couple to the stimulatory G protein $G_s$, activating adenylyl cyclase, and increasing intracellular cAMP. Through the subsequent phosphorylation of several intracellular proteins via the cAMP-dependent protein kinase A, such $\beta_1$AR activation culminates in an increase in cardiac inotropy, lusitropy and chronotropy. As previously discussed, there are two common $\beta_1$ARs in the human population due to a polymorphic variation which results in an encoded Gly or Arg at amino acid position 389 of the $G_s$ coupling domain of the receptor. In a recombinant cell-based expression system, $\beta_1$ Arg389 displays a markedly enhanced coupling to adenylyl cyclase compared to $\beta_1$Gly389. The inventors discovered that polymorphic alpha-2C individuals with both the polymorphic alpha-2C and the $\beta_1$Arg389 have the greatest risk of heart failure, since norepinephrine release and $\beta_1$AR activity are enhanced concomitantly.

The inventors have discovered that polymorphisms of the $\beta_1$AR and the $\alpha_{2C}$AR which jointly represent a potentially major risk factor for development of a cardiovascular disease. Specifically, in African-Americans, where $\alpha_{2C}$Del322-325 and $\beta_1$Arg389 are not uncommon, the $\alpha_{2C}$Del322-325 polymorphism effect alone represented some degree of risk (odds ratio=5.65), while the $\beta_1$Arg389 genotype is not associated with heart failure. However, when occurring together in the homozygous state, the risk is substantial and highly statistically significant, with an odds ratio of 10.11 (95 percent CI 2.11 to 48.53, P=0.004). Given the low prevalence of the $\alpha_{2C}$Del322-325 polymorphism in Caucasians, the inventors did not expect a significant association in this ethnic group after further subdivision by $\beta_1$AR genotype. Nevertheless, in the Caucasian subjects, the allele frequency of the $\alpha_{2C}$Del322-325 was indeed more common among heart failure patients relative to controls. Therefore, while not wishing to be bound by theory, the inventors believe that the molecular properties of the two polymorphic receptors may be a risk factor for cardiovascular disease in all individuals.

Accordingly, the inventors have discovered methods for cardiovascular disease assessment in an individual. The methods comprise the steps of detecting the presence or absence of a fragment encoding a polymorphic alpha-2C ($\alpha_{2C}$DEL322-325) adrenergic receptor in a sample from an individual; and detecting the presence or absence of a fragment encoding a polymorphic beta-1 adrenergic receptor ($\beta_1$Arg389) in a sample from the individual.

The inventors have also discovered methods for delaying development of cardiovascular disease in an individual. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\beta_1$Arg389) in a sample from the individual; and selecting a therapy regimen for the individual based on the presence or absence of $\alpha_{2C}$DEL322-325 and $\beta_1$Arg389. The therapy regimen delays development of cardiovascular disease in the individual.

The inventors have also discovered methods for delaying progression or early death associated with cardiovascular disease in an individual. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\beta_1$Arg389) in a sample from the individual; and selecting a therapy regimen for the individual based on the presence or absence of $\alpha_{2C}$DEL322-325 and $\beta_1$Arg389. Progression or early death associated with the cardiovascular disease is delayed.

The inventors have further discovered methods of genetic counseling for cardiovascular disease in an individual. The methods comprise the steps of detecting the presence or absence of a fragment encoding a polymorphic alpha-2C ($\alpha_{2C}$DEL322-325) adrenergic receptor in a sample from an individual; detecting the presence or absence of a fragment encoding a polymorphic beta-1 adrenergic receptor ($\beta_1$Arg389) in a sample from the individual; and counseling the individual regarding the potential risk of developing a cardiovascular disease based on the presence or absence of $\alpha_{2C}$DEL322-325 and $\beta_1$Arg389.

As used herein, "individual" is intended to refer to a human, including but not limited to, embryos, fetuses, children, and adults. One skilled in the art will recognize the various samples available for detecting the presence or absence of a fragment in an individual, any of which may be used herein. Samples include, but are not limited to, blood samples, tissue samples, body fluids, or combinations thereof.

As used herein, "assessment" is intended to refer to the prognosis, diagnosis, monitoring, delaying development, delaying progression, delaying early death, risk for developing, staging, predicting progression, predicting response to therapy regimen, tailoring response to a therapy regimen, predicting or directing life-style changes that alter risk or clinical characteristics, of a cardiovascular disease based upon the presence and/or absence of $\alpha_{2C}$DEL322-325 and $\beta_1$Arg389 in an individual's sample.

As used herein, "fragment" is intended to refer to a sequence of nucleic acids and/or amino acids encoding DNA, RNA, protein or combinations thereof. In one embodiment, the fragment comprises the polymorphic alpha-2C adrenergic receptor ($\alpha_{2C}$DEL322-325) or $\alpha_{2C}$DEL322-325 site. In another embodiment, the fragment comprises the wild-type alpha-2C adrenergic receptor or site. In yet another embodiment, the fragment comprises the polymorphic beta-1 adrenergic receptor ($\beta_1$Arg389) or $\beta_1$ Arg389 site. In yet another embodiment, the fragment comprises the Gly-3 89 beta-1 adrenergic receptor or site.

Cardiovascular disease includes, but is not limited to, stroke, vascular embolism, vascular thrombosis, heart failure, cardiac arrhythmias, myocardial infarction, myocardial ischemia, angina, hypertension, hypotension, shock, sudden cardiac death, or combinations thereof. In a specific embodiment, the cardiovascular disease comprises heart failure.

One skilled in the art will appreciate the various known direct and/or indirect techniques for detecting the presence or absence of a DNA and/or fragment, any of which may be used herein. Techniques include, but are not limited to, fluorescent techniques, spectroscopic method, arrays, direct sequencing, restriction site analysis, hybridization, primary-mediated primary extension, gel migration, antibody assays, or combinations thereof. One skilled in the art will appreciate the various known direct and/or indirect techniques for detecting the presence or absence of an amino acid protein fragment, any of which may be used herein. These techniques include, but are not limited to, amino acid sequencing, antibodies, Western blots, 2-dimensional gel electrophoresis, immunohistochemistry, autoradiography, or combinations thereof As used herein, “therapy regimen” is intended to refer to a procedure for delaying development, delaying progression, or delaying early death associated with a cardiovascular disease. In one embodiment, the therapy regimen comprises administration of agonists and/or antagonists of $\alpha_{2C}$DEL322-325 and $\beta_1$Arg389. In another embodiment, the therapy regimen comprises life-style changes, including, but not limited to, changes in diet, exercise, and the like.

As discussed earlier, the exploration of β, AR and $\alpha_{2c}$ AR as candidates for risk factors for heart failure is supported by results from a number of basic, animal, and human studies. $\alpha_2$AR expressed on human presynaptic cardiac sympathetic nerves inhibit the release of the neuotransmitter norepinephrine. Fore example, mice engineered to lack expression of $\alpha_{2A}$AR and $\alpha_{2C}$AR show that the $\alpha_{2C}$AR inhibits norepinephrine release under basal conditions (low stimulation frequencies). Such mice develop heart failure. Thus, these factors which depress $\alpha_{2C}$AR function leading to chronically enhanced norepinephrine release may represent factors predisposing to the development of heart failure. Moreover, factors which depress $\beta_1$AR function may also represent factors predisposing an individual to the development of heart failure.

The inventors’ results demonstrate a substantial risk of heart failure in an individual who has the homozygous $\alpha_{2C}$Del322-325 polymorphism. The inventors’ results further demonstrate that an individual has an even greater risk of heart failure when the individual has both the homozygous $\alpha_{2C}$Del322-325 polymorphism and the homozygous $\beta_1$Arg389 variant (referred to also as “the double homozygous genotype”). While not wishing to be bound by theory, the inventors believe that the interaction between the two polymorphic receptors is due to the fact that the receptors represent two critical components within a series-type signal transduction pathway: local norepinephrine production and its activation of its target receptor. The synergistic, rather than simply additive, nature of the interaction may be due to the fact that G-protein coupled receptor activation results in marked signal amplification. This is the first example of such an interaction within a discrete signaling pathway in heart failure.

The presence of the double homozygous genotype may indicate the need for specific pharmacologic therapy with $\alpha_2$AR agonists or antagonists and/or βAR agonists or antagonists. Patients with the homozygous $\alpha_{2C}$Del322-325/$\beta_1$Arg389 genotype may represent a subset of responders or non-responders, and thus genetic testing at these loci may be used to tailor pharmacologic therapy to those with the greatest likelihood of having a favorable outcome. Moreover, while not wishing to be bound by theory, the inventors believe that such individuals may benefit from treatment early in the syndrome, even with relatively preserved cardiac function and minimal symptoms, since they may be at greatest risk of progression. A similar approach may also be indicated in individuals with asymptomatic left ventricular hypertrophy, with the objective of halting transition to clinical heart failure. Finally, individuals without hypertrophy or failure who have the double homozygous genotype, and are thus at risk for developing heart failure, may also benefit from “prophylactic therapy.”

EXAMPLE

Subjects

The protocol is approved by the University of Cincinnati Institutional Review Board, and subjects provide written informed consent. Normal (control) individuals and heart failure patients are from the greater Cincinnati geographic area. Patients are recruited from the University of Cincinnati Heart Failure Program (Jan. 2, 1999-Jan. 2, 2001) by requests of consecutive eligible patients who agree to participate in this specific genetic study. Approximately 50 percent of patients in the Program are referred by community cardiologists, ~40 percent by physicians within this tertiary care center, and ~10 percent self-referred.

To limit sample data, entry criteria are ages 20-79, left ventricular ejection fractions (LVEF) of <35 percent, NYHA II-IV heart failure, and either idiopathic dilated cardiomyopathy or ischemic cardiomyopathy. Patients with a non-ischemic dilated cardiomyopathy who had antecedent hypertension are characterized as idiopathic. To further limit the sample size, patients whose heart failure is due to primary valvular disease, myocarditis, or obstructive or hypertrophic cardiomyopathies, are not eligible due to the limited number of cases. The control group consists of unrelated, apparently healthy individuals (as assessed by questionnaire) recruited prior to voluntary blood donation and by newspaper advertisements. Specifically, none of the control group has a history of cardiovascular disease or symptoms, or are taking any chronic medications. The racial classification of the participants is self-reported.

Genotyping

Genotyping at these loci is carried out in 171 patients with heart failure and 193 control subjects. Logistic regression methods are utilized to determine the potential effect of each genotype, and their interaction, on the risk of heart failure. In another group of 261 patients with heart failure, analysis was carried out to assess the relationship between genotype and the duration of heart failure. In another group of 263 patients with heart failure, analysis was carried out to assess the risk of hypertension. Genotypes at 9 highly polymorphic short tandem repeat loci are used to test for population stratification between cases and controls within ethnic groups.

Genomic DNA is extracted from peripheral blood samples, and the adrenergic receptor polymorphisms are detected. The adrenergic genotypes are referred to as wild-type $\alpha_{2C}$AR (representing the more common variant that does not have the deletion), $\alpha_{2C}$Del322-325 (the four amino acid deletion variant), $\beta_1$Arg389 and $\beta_1$Gly389. Both sequence analysis and restriction enzyme digestion of PCR products spanning the $\alpha_{2C}$AR (see FIG. 3) or $\beta_1$AR polymorphisms (see FIG. 4) are used to detect each sequence variant in! genomic DNA samples.

Figure 3:
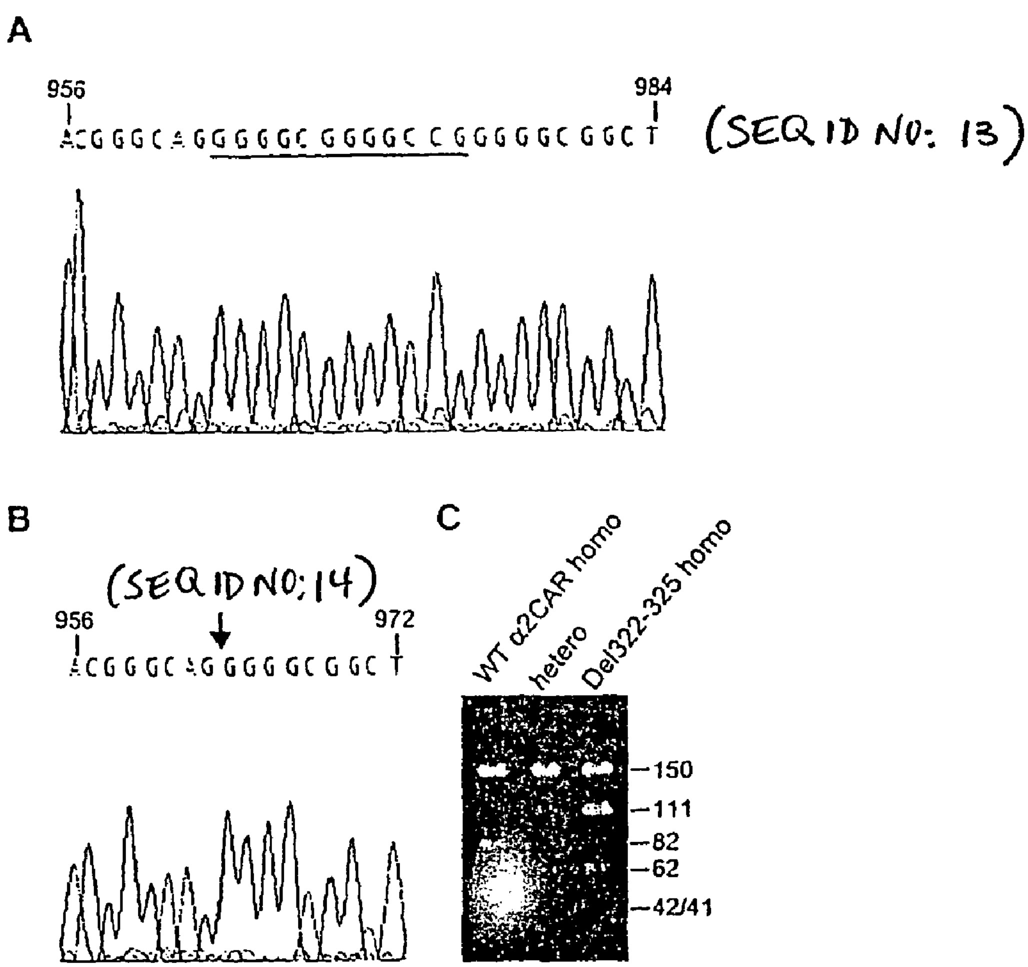
FIGS. 3A and 3B depict sequence analysis of PCR products spanning the alpha-2C adrenergic receptor.
FIG. 3C depicts restriction enzyme digestion of PCR products spanning the alpha-2C adrenergic receptor.

FIG. 3 shows sequencing electropherograms (sense strand) that identify homozygous individuals for the wild-type and Del322-325 $\alpha_{2C}$AR. Nucleotides 964-975 (GGGGCGGGGCCG) within the wild-type sequence (FIG. 3A) are absent in the Del322-325 sequence (FIG. 3B). In addition, deletion of these 12 nucleotides results in loss of one of six Nci I restriction enzyme sites within a 372 bp PCR product amplified from genomic DNA samples. Agarose gel electrophoresis of PCR products digested with Nci I therefore show unique patterns of fragments that identify homozygous wild-type, homozygous Del322-325, and heterozygous individuals (FIG. 3C).

Figure 4:
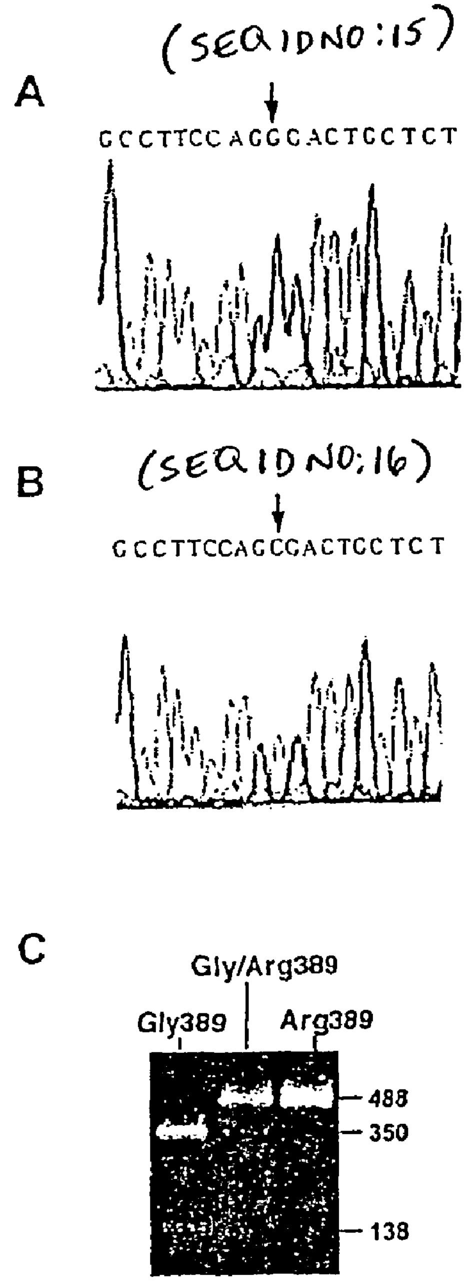
FIGS. 4A and 4B depict sequence analysis of PCR products spanning the beta-1 adrenergic receptor.
FIG. 4C depicts restriction enzyme digestion of PCR products spanning the beta-1 adrenergic receptor.

FIG. 4 shows sequencing electropherograms (sense strand) that identify homozygous individuals for the $\beta_1$AR Gly389 or Arg389 polymorphism with either a G or a C at nucleotide position 1165, respectively. The presence of a C in this position results in loss of a BsmFI restriction enzyme site, therefore BsmFI digestion and agarose gel electrophoresis of 488 bp PCR products spanning this polymorphic site identified all three genotypes (heterozygous, homozygous Gly389 and homozygous Arg389).

In combination, the above methods are used to determine all $\beta_1$AR/$\alpha_{2C}$AR genotypes, including the two-locus allele frequencies of the $\beta_1$AR Arg389 and Del322-325 $\alpha_{2C}$AR polymorphisms in cases and controls.

Figure 2:
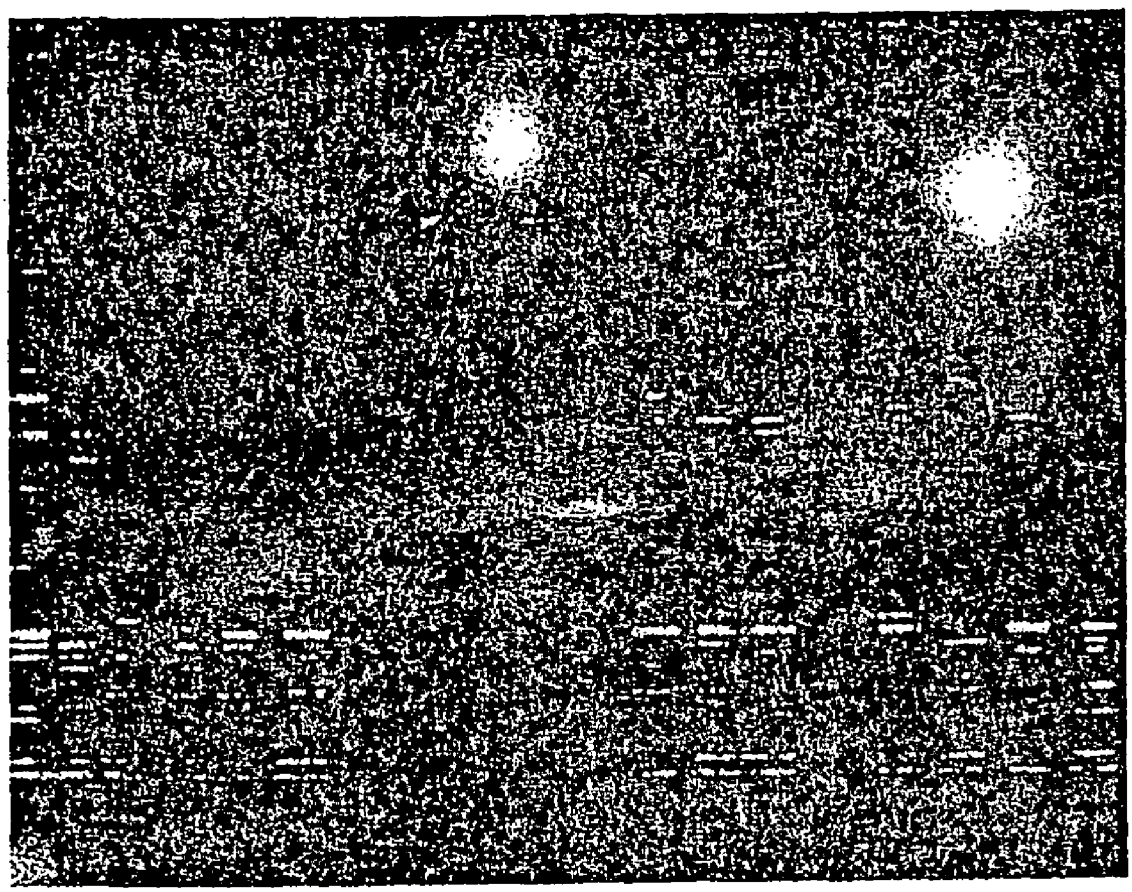

To assess the potential for population stratification, the frequencies of alleles at nine highly polymorphic short tandem repeat (STR) loci are determined by a multiplexed PCR using the AmpFlSTR reagents with detection by multicolor fluorescence using the ABI Prism 377 Sequencer (Applied BioSystems), as illustrated in FIG. 2.

Statistical Analysis

Allele frequencies are computed using standard gene counting methods. Tests for genotype and allelic association with heart failure are conducted using chi-square tests of independence within each ethnic group. In order to test for interactions between the $\alpha_{2C}$AR and $\beta_1$AR polymorphisms, the inventors use logistic regression methods to model the effect of each genotype and their interaction on the risk of heart failure. Likelihood ratio tests are used to assess the significance of each locus and their interaction both before and after adjusting for the potential confounding effects of age and sex.

Finally, a case-only analysis is performed to test for single and two-locus genotype associations with hypertension status and diagnosis group (idiopathic or ischemic) using chi-square tests of independence. The frequencies of the STR alleles are compared between cases and controls within the two racial groups by chi-square tests. When appropriate, mean data are reported±standard deviation. Kaplan-Meier plots and log-rank tests are used to assess whether the survival distribution differed significantly across genotype classes.

Results

In African-Americans, the adjusted odds of heart failure is 5.65 times higher in the $\alpha_{2C}$Del322-325 homozygotes (95 percent confidence interval: 2.67 to 11.95, P<0.0001) relative to the other $\alpha_{2C}$AR genotypes. There is no risk with $\beta_1$Arg389 alone. However, there is a marked increased risk of heart failure in individuals homozygous for both variants: adjusted odds ratio=10.11 (95 percent confidence interval: 2.11 to 48.53, P=0.004). This association holds with dilated and ischemic cardiomyopathy, and is independent of antecedent hypertension. The frequencies of the short tandem repeat alleles are not different between cases and controls, thus excluding population stratification. In Caucasians, the $\alpha_{2C}$Del322-325 polymorphism is also associated with heart failure (allele frequency 0.105 vs 0.038 in controls, p=0.0l 1). However, there are too few patients with both homozygous genotypes to adequately assess the risk.

The characteristics of the heart failure cases are shown in Table 2. For African-Americans there are 78 patients (49±11 years of age) and 84 controls (53±16 years of age). There are 81 Caucasian heart failure patients who are 56±11 years of age and 105 controls whose ages are 36±12. There are significant differences in allele frequencies of both receptor variants between African-Americans and Caucasians. In the current study the $\alpha_{2C}$Del322-325 is found to be >10 times more common in African-American compared to Caucasian controls (allele frequencies of 0.411 vs 0.038, P<0.0001). The $\beta_1$Arg389 is somewhat less common in African-Americans (0.560 vs 0.762, P<0.0001). These differences in the frequencies of the two polymorphisms between Caucasians and African-Americans, particularly at the $\alpha_{2C}$Del322-325 locus, prompted the inventors to carry out separate risk analyses for the two ethnic groups.

In African-Americans, where both variants are relatively common, single-locus analysis, as detailed in Table 3, reveals that $\alpha_{2C}$Del322-325 is in fact more common in patients with heart failure (allele frequency=0.615) compared to normal controls (allele frequency=0.411, P=0.0002). When analyzed using all three possible genotypes, this association remains highly significant. Indeed, 53 percent of African-Americans with heart failure are homozygous for the polymorphism compared to only 17 percent of the controls. The unadjusted odds ratio for heart failure and the homozygous $\alpha_{2C}$Del322-325 is 5.54 (95 percent confidence interval: 2.68 to 11.45, P<0.0001). There is no evidence of significant confounding by age or sex, and the confounder adjusted odds ratio for heart failure and the homozygous $\alpha_{2C}$Del322-325 is 5.65 (95 percent confidence interval: 2.67 to 11.95, P<0.0001). In contrast to the $\alpha_{2C}$AR polymorphism, there is no evidence of a statistically significant difference in the allele frequencies of $\beta_1$Arg389 in African-Americans with or without heart failure.

A two-locus analysis indicates a significant interaction between the $\alpha_{2C}$Del322-325 and the $\beta_1$Arg389 genotypes in African-Americans with heart failure. The combination reveals a multiplicative association (i.e. greater than an additive effect) of the two loci with risk of heart failure (likelihood ratio test for interaction P=0.05). Subjects are placed into four groups as follows: homozygous for both $\alpha_{2C}$Del322-325 and $\beta_1$Arg389; homozygous for $\alpha_{2C}$Del322-325 only; homozygous for the $\beta_1$Arg389 only; and non-homozygous for both (referent genotype class). Results are shown in Table 4 and reveal that homozygosity for $\alpha_{2C}$Del322-325 and $\beta_1$Arg389 is associated with a substantial increased risk for heart failure in African-Americans (unadjusted odds ratio=12.67, 95 percent confidence interval: 2.70 to 59.42, P=0.001), relative to the referent genotype class. When age and sex are controlled for in the model, the odds ratio is slightly reduced but remains highly statistically significant (adjusted odds ratio=10.11, 95 percent confidence interval: 2.11 to 48.53, P=0.004).

To assess whether these findings could be explained by two-locus genotype by diagnosis group (idiopathic dilated and ischemic cardiomyopathy) or hypertension status distributional differences among the cases, a case-only analysis is performed. Among the African-American cases, there are no two-locus genotype frequency differences between the two diagnosis types (chi-square=1.38, P=0.71) or hyper- and normotensive patients (chi-square=0.3357, P=0.95).

In Caucasians, the inventors discovered that the allele frequency of $\alpha_{2C}$Del322-325 in heart failure patients is higher than controls (0.105 vs 0.038, P=0.01 1) (see Table 3). The difference in significance levels is likely due to the small number of Caucasian subjects in the $\alpha_{2C}$Del322-325 homozygote group (2 normals and 6 cases). As is seen with the African-Americans, the frequency of the $\beta_1$Arg389 is not different between cases and controls in Caucasians. There is no significant association found with the two-locus model and the risk of heart failure in Caucasians; however there is a strong trend towards the double homozygous genotype being a risk factor for heart failure in Caucasians, since it occurred in 1.9% in normals and 3.7% in heart failure patients. It is contended that the association would attain statistical significance with larger number of patients studied.

The potential for unrecognized population stratification between control and heart failure groups, which could result in a spurious association in the African-Americans, is explored by genotyping at nine highly polymorphic STR loci, illustrated in Table 5. (Of note, since all subjects are from the same geographic area and associations are sought within racial groups, the likelihood of population stratification is considered to be low.) Control and heart failure subjects within the African-Americans show no differences in the frequencies at these markers (see P-values in Table 5), indicating that population stratification between cases and controls does not account for our association findings.

Finally, the unlikely possibility of a biased result in African-Americans, where there were sufficient numbers of patients, is considered using contingency tables. The ages at time of enrollment into the study are not different between those with the various $\alpha_{2C}$AR genotypes. However the odds of failure developing before age 40 is 4.07 times higher (95 percent confidence interval: 1.25 to 13.30, P=0.023) for $\alpha_{2C}$Del322-325 carriers compared to those homozygous for wild-type $\alpha_{2C}$AR. Further analysis utilizes the median LVEF for all African-American patients (which is 22.0 percent) to define two groups with different predicted mortalities. The odds of having an LVEF ≦22 percent is 3.63 times higher (95 percent confidence interval: 1.17 to 11.22, P=0.03) for $\alpha_{2C}$Del322-325 homozygotes compared to those homozygous for wild-type $\alpha_{2C}$AR. In addition, while not wishing to be bound by theory, other studies suggest that presence of the Del322-325 polymorphism may predict survival. In this case, analyses is performed on patients (n=4) who died or underwent heart transplantation during the course of the study. Within this group, the median duration of heart failure, defined as the age at death or transplant minus the age at onset, is shorter in patients homozygous for Del322-325 (4.1 years) compared to homozygous wild-type $\alpha_{2C}$AR (4.8 years). These results do not suggest a “survivor effect” and support the conclusion that it is the $\alpha_{2C}$Del322-325 allele, as opposed to the wild-type $\alpha_{2C}$AR, that is associated with the failure phenotype. Furthermore, since the above analysis is carried out, by necessity, only in those with heart failure, these results indicate that the $\alpha_{2C}$DEL322-325 has not only an effect on risk, but also identifies patients with an early-onset form of the disease, and patients with a more severe form of the disease. The odds of failure developing before age 40 is 4.07 times higher (95 percent confidence interval: 1.25 to 13.30, P=0.023) for $\alpha_{2C}$DEL322-325 carriers compared to those homozygous for wild-type $\alpha_{2C}$AR. The odds of having an LVEF ≦22 percent is 3.63 times higher (95 percent confidence interval: 1.17 to 11.22, P=0.03) for $\alpha_{2C}$DEL322-325 homozygotes compared to those homozygous for wild-type $\alpha_{2C}$AR. As indicated, both of these associations are statistically significant. For the $\beta_1$Arg389, a larger cohort of heart failure patients (n=216) that died or were transplanted following enrollment are examined. Again, while not wishing to be bound by theory, the duration of heart failure (years to heart transplant or death) is shorter in individuals homozygous for the polymorphic Arg-389 receptor (4.0 years) compared to individuals homozygous for the wild-type Gly-389 receptor (5.6 years). In an additional analysis of 263 patients with heart failure, an association with $\beta_1$AR genotype and hypertension is noted. Here, the mean ±standard error systolic blood pressure is 110±3.7 mmHg for patients who are homozygous for $\beta_1$Gly389, 114±1.8 mmHG for those who are heterozygous, and 122±1.8 mmHg for those homozygous for $\beta_1$Arg389. These data show that these variants can be used to assess risk for hypertension, and, they can serve to modify heart failure through this effect, since hypertension can cause a worsening of ventricular function in heart failure.

TABLE 2

Characteristics of the heart failure groups.

| | Caucasian | African-American |
|---|---|---|
| Age (y) | 54.6 ± 11.1 | 48.9 ± 11.5 |
| Gender (% male) | 76.5 | 59.0 |
| NYHA class (% III or IV) | 47.5 | 47.4 |
| Diagnosis (%) | | |
| Idiopathic | 45.7 | 83.3 |
| Ischemic | 54.3 | 16.7 |
| Age of onset (y) | 51.7 ± 10.7 | 46.3 ± 11.8 |
| Duration (y) | 2.62 ± 4.35 | 2.62 ± 4.77 |
| LVEF at enrollment (%) | 24.8 ± 12.6 | 25.4 ± 11.9 |
| Expired after enrollment (%) | 25.9 | 26.9 |
| Transplanted after enrollment (%) | 14.8 | 9.0 |
| Other risk factors/co-morbid conditions (%) | | |
| hypertension (≧140/90) | 44.8 | 61.0 |
| diabetes mellitus | 30.9 | 25.6 |
| hypercholesterolemia history (≧240 mg/dL) | 44.4 | 23.1 |
| obesity (BMI >25 kg/m$^2$) | 72.5 | 66.2 |
| Smoking (%) | | |
| (history pk yrs ≧10) | 70.8 | 58.6 |
| concurrent | 17.5 | 23.4 |
| Medications at entry (%) | | |
| digoxin | 76.5 | 50.0 |
| diuretic | 91.4 | 56.4 |
| ACE inhibitor | 82.7 | 92.3 |
| β-blocker | 60.5 | 33.3 |

TABLE 3

Distribution of $\alpha_2$- and $\beta_1$-adrenergic receptor variants in normal and heart failure subjects.

| | Allele frequency | P-value* by allele | Genotype† # of subjects (%) | | | P-value‡ by genotype | odds ratio§ (95% confidence interval) |
|---|---|---|---|---|---|---|---|
| $\alpha_{2C}$Del322-325 | Del | | WT/WT | WT/Del | Del/Del | | |
| African-Americans | | | | | | | |
| Normal | 0.411 | 0.0002 | 29 (34.5) | 41 (48.8) | 14 (16.6) | <0.0001 | 5.65 |
| Heart failure | 0.615 | | 23 (29.5) | 14 (17.9) | 41 (52.5) | | (2.67 to 11.95) |
| Caucasians | | | | | | | |
| Normal | 0.038 | 0.011 | 99 (94.3) | 4 (3.8) | 2 (1.9) | 0.132 | 3.94 |
| Heart failure | 0.105 | | 70 (86.4) | 5 (6.2) | 6 (7.4) | | (0.50 to 31.05) |
| $\beta_1$Arg389 | Arg | | Gly/Gly | Gly/Arg | Arg/Arg | | |
| African-Americans | | | | | | | |
| Normal | 0.560 | 0.541 | 13 (15.5) | 48 (57.1) | 23 (27.4) | 0.270 | 0.90 |
| Heart failure | 0.526 | | 19 (24.4) | 36 (46.2) | 23 (29.4) | | (0.44 to 1.84) |
| Caucasians | | | | | | | |
| Normal | 0.762 | 0.640 | 8 (7.6) | 34 (32.4) | 63 (60.0) | 0.360 | 0.80 |
| Heart failure | 0.741 | | 4 (4.9) | 34 (42.0) | 43 (53.1) | | (0.37 to 1.73) |

*2 × 2 - chi-square comparing number of alleles in the normal vs heart failure groups.
†WT, wild-type $\alpha_{2C}$AR (without the deletion); Del, $\alpha_{2C}$Del322-325
‡2 × 3 chi-square test comparing the distribution of the three possible genotypes in the normal vs heart failure groups.
§Sex and age adjusted odds ratio for the association of heart failure with genotype (Arg/Arg vs Gly/Gly and Gly/Arg; or Del/Del vs WT/WT and WT/Del.

TABLE 4

Gene-gene interactions of $\alpha_2$- and $\beta_1$-adrenergic receptor variants in heart failure.

| $\alpha_{2C}$AR | $\beta_1$AR | Number of Subjects: Normal | Number of Subjects: Heart failure | Odds ratio* (95% CI; P-value) |
|---|---|---|---|---|
| African-American | | 84 | 78 | |
| ≧1 WT | ≧1 Gly389 | 49 | 29 | 1.00 (reference) |
| ≧1 WT | Arg389/Arg389 | 21 | 8 | 0.55 (0.21 to 1.44; P = 0.226) |
| Del322-325/Del322-325 | ≧1 Gly389 | 12 | 26 | 3.87 (1.65 to 9.05; P = 0.002) |
| Del322-325/Del322-325 | Arg389/Arg389 | 2 | 15 | 10.11 (2.11 to 48.53; P = 0.004) |
| Caucasian | | 105 | 81 | |
| ≧1 WT | ≧1 Gly389 | 42 | 35 | 1.00 (reference) |
| ≧1 WT | Arg389/Arg389 | 61 | 40 | 0.85** (0.39 to 1.85; P = 0.682) |
| Del322-325/Del322-325 | ≧1 Gly389 | 0 | 3 | undefined |
| Del322-325/Del322-325 | Arg389/Arg389 | 2 | 3 | 2.14** (0.13 to 36.85, P = 0.60) |

*Odds ratios adjusted for sex and age.
**Due to the cell with 0 subjects, these odds ratios represent single (2 × 2) comparisons with the reference genotype

TABLE 5

Frequencies of short tandem repeat alleles in cases and controls*

| | Caucasian Control | Caucasian Heart Failure | African-American Control | African-American Heart Failure |
|---|---|---|---|---|
| | | D3S1358- | | |
| 14 | 0.094 | 0.164 | 0.150 | 0.127 |
| 15 | 0.344 | 0.250 | 0.250 | 0.227 |
| 16 | 0.240 | 0.250 | 0.381 | 0.340 |
| 17 | 0.146 | 0.184 | 0.169 | 0.240 |
| all other | 0.177 | 0.151 | 0.050 | 0.067 |
| | | vWA- | | |
| 14 | 0.146 | 0.110 | 0.099 | 0.093 |
| 15 | 0.083 | 0.104 | 0.191 | 0.193 |
| 16 | 0.229 | 0.182 | 0.276 | 0.233 |
| 17 | 0.240 | 0.273 | 0.237 | 0.220 |
| 18 | 0.167 | 0.214 | 0.105 | 0.100 |
| 19 | 0.115 | 0.097 | 0.033 | 0.067 |
| all other | 0.02 | 0.019 | 0.059 | 0.093 |
| | | FGA- | | |
| 19 | 0.053 | 0.061 | 0.068 | 0.074 |
| 20 | 0.128 | 0.061 | 0.041 | 0.101 |
| 21 | 0.181 | 0.142 | 0.103 | 0.122 |
| 22 | 0.202 | 0.264 | 0.171 | 0.169 |
| 23 | 0.117 | 0.162 | 0.178 | 0.169 |
| 24 | 0.149 | 0.169 | 0.171 | 0.149 |
| 25 | 0.128 | 0.088 | 0.096 | 0.108 |
| 27 | 0.0 | 0.02 | 0.062 | 0.020 |
| all other | 0.043 | 0.034 | 0.110 | 0.088 |
| | | D8S1179- | | |
| 12 | 0.125 | 0.132 | 0.094 | 0.107 |
| 13 | 0.365 | 0.309 | 0.163 | 0.253 |
| 14 | 0.219 | 0.184 | 0.394 | 0.387 |
| 15 | 0.104 | 0.105 | 0.231 | 0.153 |
| 16 | 0.052 | 0.026 | 0.050 | 0.047 |
| all other | 0.135 | 0.244 | 0.069 | 0.053 |
| | | D21S11- | | |
| 27 | 0.031 | 0.046 | 0.094 | 0.067 |
| 28 | 0.167 | 0.158 | 0.206 | 0.240 |
| 29 | 0.198 | 0.263 | 0.175 | 0.240 |
| 30 | 0.240 | 0.217 | 0.125 | 0.153 |

TABLE 5-continued

Frequencies of short tandem repeat alleles in cases and controls*

| | Caucasian Control | Caucasian Heart Failure | African-American Control | African-American Heart Failure |
|---|---|---|---|---|
| 31 | 0.094 | 0.039 | 0.100 | 0.067 |
| 31.2 | 0.104 | 0.104 | 0.050 | 0.040 |
| 32.2 | 0.083 | 0.092 | 0.119 | 0.067 |
| all other | 0.083 | 0.159 | 0.131 | 0.127 |
| 12 | 0.138 | 0.167 | 0.056 | 0.081 |
| 13 | 0.128 | 0.080 | 0.056 | 0.068 |
| 14 | 0.234 | 0.147 | 0.056 | 0.054 |
| 15 | 0.160 | 0.160 | 0.160 | 0.182 |
| 16 | 0.106 | 0.127 | 0.215 | 0.182 |
| 17 | 0.085 | 0.113 | 0.090 | 0.182 |
| 18 | 0.021 | 0.093 | 0.118 | 0.095 |
| 19 | 0.021 | 0.020 | 0.132 | 0.088 |
| all other | 0.107 | 0.094 | 0.118 | 0.068 |
| | | D5S818- | | |
| 8 | 0.0 | 0.007 | 0.063 | 0.033 |
| 10 | 0.073 | 0.053 | 0.050 | 0.040 |
| 11 | 0.333 | 0.375 | 0.263 | 0.227 |
| 12 | 0.344 | 0.336 | 0.294 | 0.407 |
| 13 | 0.198 | 0.171 | 0.275 | 0.240 |
| all other | 0.052 | 0.059 | 0.056 | 0.053 |
| | | D135317- | | |
| 11 | 0.302 | 0.336 | 0.272 | 0.304 |
| 12 | 0.271 | 0.303 | 0.418 | 0.466 |
| 13 | 0.094 | 0.099 | 0.146 | 0.108 |
| all other | 0.334 | 0.263 | 0.165 | 0.122 |
| | | D7S820- | | |
| 8 | 0.094 | 0.133 | 0.230 | 0.264 |
| 9 | 0.146 | 0.207 | 0.079 | 0.074 |
| 10 | 0.302 | 0.240 | 0.316 | 0.311 |
| 11 | 0.240 | 0.193 | 0.243 | 0.257 |
| 12 | 0.146 | 0.153 | 0.099 | 0.054 |
| all other | 0.073 | 0.074 | 0.033 | 0.041 |

Comparison of frequencies of each allele revealed P values all >0.05 between control and heart failure patients within the two racial groups.

What is claimed is:

1. A method for cardiovascular disease assessment in an individual, comprising the steps of:

a. detecting the presence or absence of a deletion of amino acids 322-355 in an alpha-2C adrenergic receptor ($\alpha_{2C}$DEL322-325) in a sample from an individual;

b. detecting the presence or absence of an arginine at position 389 of a beta-1 adrenergic receptor ($\beta_1$Arg389) in a sample from the individual; and c. if both a homozygous $\alpha_{2C}$DEL322-325 polymorphism is present and homozygous $\beta_1$Arg389 polymorphism is present, assessing that the individual is at increased risk for heart failure.

2. The method according to claim 1, wherein the sample comprises a blood sample, body fluid, tissue sample, or combinations thereof.

3. The method according to claim 1, wherein at least one of the detecting steps is performed using a nucleic acid assay or a protein assay.

4. The method of claim 1, further comprising the step of selecting a therapy regimen for the individual based on the presence of both the $\alpha_{2c}$DEL322-325 polymorphism and the $\beta_1$Arg389 polymorphism, wherein the therapy regimen delays development of heart failure in the individual.

5. The method according to claim 4, wherein the therapy regimen comprises administration of an agonist of $\alpha_{2c}$DEL322-325, an antagonist of $\beta_1$Arg389, or both.

6. The method according to claim 4, wherein the therapy regimen comprises life-style changes.

7. The method of claim 1, further comprising the step of selecting a therapy regimen for the individual based on the presence of both the $\alpha_{2c}$DEL322-325 polymorphism and the $\beta_1$Arg389 polymorphism, wherein the therapy regimen delays early death associated with the heart failure.

8. The method of claim 1, further comprising the step of counseling the individual regarding the potential risk of developing a heart failure based on the presence of both the $\alpha_{2c}$DEL322-325 polymorphism and the $\beta_1$Arg389 polymorphism.

* * * * *

UNITED STATES PATENT AND TRADEMARK OFFICE

CERTIFICATE OF CORRECTION

PATENT NO. : 7,642,052 B2
APPLICATION NO. : 10/527263
DATED : January 5, 2010
INVENTOR(S) : Kersten M. Small et al.

It is certified that error appears in the above-identified patent and that said Letters Patent is hereby corrected as shown below:

In column 1, lines 15-19, delete
"This invention was made, at least in part, with funds from the Federal Government, awarded through grant numbers NIH HL-52318 (SCOR in Heart Failure), ES-06096 and HG-00040. The U.S. Government therefor has certain acknowledged rights to the invention." and insert
--This invention was made with government support under grant numbers HL-52318, ES-06096, and HG-00040 awarded by the National Institutes of Health. The government has certain rights in the invention.-- therefor.

In claim 1, column 35, line 36, delete "cardiovascular disease" and insert
--heart failure-- therefor.

In claim 1, column 35, line 39, delete "355" and insert --325-- therefor.

In claim 1, column 35, line 45, between "and" and "homozygous", insert --a--.

Signed and Sealed this

Thirtieth Day of March, 2010

David J. Kappos
*Director of the United States Patent and Trademark Office*

UNITED STATES PATENT AND TRADEMARK OFFICE

CERTIFICATE OF CORRECTION

PATENT NO. : 7,642,052 B2
APPLICATION NO. : 10/527263
DATED : January 5, 2010
INVENTOR(S) : Small et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this

Sixteenth Day of November, 2010

David J. Kappos

David J. Kappos
*Director of the United States Patent and Trademark Office*

UNITED STATES PATENT AND TRADEMARK OFFICE

CERTIFICATE OF CORRECTION

PATENT NO. : 7,642,052 B2
APPLICATION NO. : 10/527263
DATED : January 5, 2010
INVENTOR(S) : Kersten M. Small and Stephen B. Liggett It is certified that error appears in the above-identified patent and that said Letters Patent is hereby corrected as shown below:

In the Specification

At Column 1, line 16-19, paragraph [0002], please replace the entire paragraph with the following paragraph:

This invention was made with government support under HL-52318 (SCOR in Heart Failure), ES-06096, and HG-00040 awarded by National Institutes of Health. The government has certain rights in the invention.

Signed and Sealed this
Twelfth Day of May, 2015

Michelle K. Lee

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 1389
<212> TYPE: DNA
<213> ORGANISM: homo sapiens

<400> SEQUENCE: 1

atggcgtccc cggcgctggc ggcggcgctg gcggtggcgg cagcggcggg ccccaatgcg      60

agcggcgcgg gcgagagggg cagcggcggg gttgccaatg cctcgggggc ttcctggggg     120

ccgccgcgcg gccagtactc ggcgggcgcg gtggcagggc tggctgccgt ggtgggcttc     180

ctcatcgtct tcaccgtggt gggcaacgtg ctggtggtga tcgccgtgct gaccagccgg     240

gcgctgcgcg cgccacagaa cctcttcctg gtgtcgctgg cctcggccga catcctggtg     300

gccacgctgg tcatgccctt ctcgttggcc aacgagctca tggcctactg gtacttcggg     360

caggtgtggt gcggcgtgta cctggcgctc gatgtgctgt tttgcacctc gtcgatcgtg     420
```

-continued

```
catctgtgtg ccatcagcct ggaccgctac tggtcggtga cgcaggccgt cgagtacaac    480

ctgaagcgca caccacgccg cgtcaaggcc accatcgtcg ccgtgtggct catctcggcc    540

gtcatctcct tcccgccgct ggtctcgctc taccgccagc ccgacggcgc cgcctacccg    600

cagtgcggcc tcaacgacga gacctggtac atcctgtcct cctgcatcgg ctccttcttc    660

gcgccctgcc tcatcatggg cctggtctac gcgcgcatct accgagtggc caagctgcgc    720

acgcgcacgc tcagcgagaa gcgcgccccc gtgggccccg acggtgcgtc cccgactacc    780

gaaaacgggc tgggcgcggc ggcaggcgca ggcgagaacg ggcactgcgc gccccccgccc    840

gccgacgtgg agccggacga gagcagcgca gcggccgaga ggcggcggcg ccggggcgcg    900

ttgcggcggg gcgggcggcg gcgagcgggc gcggaggggg gcgcgggcgg tgcggacggg    960

cagggggcgg ggccggggc ggctgagtcg ggggcgctga ccgcctccag gtccccgggg   1020

cccggtggcc gcctctcgcg cgccagctcg cgctccgtcg agttcttcct gtcgcgccgg   1080

cgccgggcgc gcagcagcgt gtgccgccgc aaggtggccc aggcgcgcga gaagcgcttc   1140

acctttgtgc tggctgtggt catgggcgtg ttcgtgctct gctggttccc cttcttcttc   1200

agctacagcc tgtacggcat ctgccgcgag gcctgccagg tgcccggccc gctcttcaag   1260

ttcttcttct ggatcggcta ctgcaacagc tcgctcaacc cggtcatcta cacggtcttc   1320

aaccaggatt tccggcgatc ctttaagcac atcctcttcc gacggaggag aaggggcttc   1380

aggcagtga                                                          1389
```

<210> SEQ ID NO 2
<211> LENGTH: 12
<212> TYPE: DNA
<213> ORGANISM: homo sapiens

<400> SEQUENCE: 2

```
ggggcggggc cg                                                        12
```

<210> SEQ ID NO 3
<211> LENGTH: 1360
<212> TYPE: DNA
<213> ORGANISM: homo sapiens

<400> SEQUENCE: 3

```
atggcgtccc cggcgctggc ggcggcgctg gcggtggcgg cagcggcggg ccccaatgcg     60

agcggcgcgg gcgagagggg cagcggcggg gttgccaatg cctcgggggc ttcctggggg    120

ccgccgcgcg gccagtactc ggcgggcgcg gtggcagggc tggctgccgt ggtgggcttc    180

ctcatcgtct tcaccgtggt gggcaacgtg ctggtggtga tcgccgtgct gaccagccgg    240

gcgctgcgcg cgccacagaa cctcttcctg gtgtcgctgg cctcggccga catcctggtg    300

gccacgctgg tcatgccctt ctcgttggcc aacgagctca tggcctactg gtacttcggg    360

caggtgtggt gcggcgtgta cctggcgctc gatgtgctgt tttgcacctc gtcgatcgtg    420

catctgtgtg ccatcagcct ggaccgctac tggtcggtga cgcaggccgt cgagtacaac    480

ctgaagcgca caccacgccg cgtcaaggcc accatcgtcg ccgtgtggct catctcggcc    540

gtcatctcct tcccgccgct ggtctcgctc taccgccagc ccgacggcgc cgcctacccg    600

cagtgcggcc tcaacgacga gacctggtac atcctgtcct cctgcatcgg ctccttcttc    660

gcgccctgcc tcatcatggg cctggtctac gcgcgcatct accgagtggc caagctgcgc    720

acgcgcacgc tcagcgagaa gcgcgccccc gtgggccccg acggtgcgtc cccgactacc    780
```

-continued

```
gaaaacgggc tgggcgcggc ggcaggcgca ggcgagaacg ggcactgcgc gcccccgccc     840

gccgacgtgg agccggacga gagcagcgca gcggccgaga ggcggcggcg ccggggcgcg     900

ttgcggcggg gcgggcggcg gcgagcgggc gcggaggggg gcgcgggcgg tgcggacggg     960

cagggggcgg ctgagtcggg ggcgctgacc gcctccaggt ccccggggcc cggtggccgc    1020

ctctcgcgcg ccagctcgcg ctccgtcgag ttcttcctgt cgcgccggcg ccgggcgcgc    1080

agcagcgtgt gccgccgcaa ggtggcccag gcgcgcgaga agcgcttcac ctttgtgctg    1140

gctgtggtca tgggcgtgtt cgtgctctgc tggttcccct tcttcttcag ctacagcctg    1200

tacggcatct gccgcgaggc ctgccaggtg cccggcccgc tcttcaagtt cttcttctgg    1260

atcggctact gcaacagctc gctcaacccg gtcatctaca cggtcttcaa ccaggatttc    1320

cggcgatcct ttaagcacat cctcttccga cggaggagaa                          1360


<210> SEQ ID NO 4
<211> LENGTH: 12
<212> TYPE: DNA
<213> ORGANISM: homo sapiens

<400> SEQUENCE: 4

ggggcggctg ag                                                          12


<210> SEQ ID NO 5
<211> LENGTH: 462
<212> TYPE: PRT
<213> ORGANISM: homo sapiens

<400> SEQUENCE: 5

Met Ala Ser Pro Ala Leu Ala Ala Ala Leu Ala Val Ala Ala Ala Ala
1               5                   10                  15

Gly Pro Asn Ala Ser Gly Ala Gly Glu Arg Gly Ser Gly Gly Val Ala
            20                  25                  30

Asn Ala Ser Gly Ala Ser Trp Gly Pro Pro Arg Gly Gln Tyr Ser Ala
        35                  40                  45

Gly Ala Val Ala Gly Leu Ala Ala Val Val Gly Phe Leu Ile Val Phe
    50                  55                  60

Thr Val Val Gly Asn Val Leu Val Val Ile Ala Val Leu Thr Ser Arg
65                  70                  75                  80

Ala Leu Arg Ala Pro Gln Asn Leu Phe Leu Val Ser Leu Ala Ser Ala
                85                  90                  95

Asp Ile Leu Val Ala Thr Leu Val Met Pro Phe Ser Leu Ala Asn Glu
            100                 105                 110

Leu Met Ala Tyr Trp Tyr Phe Gly Gln Val Trp Cys Gly Val Tyr Leu
        115                 120                 125

Ala Leu Asp Val Leu Phe Cys Thr Ser Ser Ile Val His Leu Cys Ala
    130                 135                 140

Ile Ser Leu Asp Arg Tyr Trp Ser Val Thr Gln Ala Val Glu Tyr Asn
145                 150                 155                 160

Leu Lys Arg Thr Pro Arg Arg Val Lys Ala Thr Ile Val Ala Val Trp
                165                 170                 175

Leu Ile Ser Ala Val Ile Ser Phe Pro Pro Leu Val Ser Leu Tyr Arg
            180                 185                 190

Gln Pro Asp Gly Ala Ala Tyr Pro Gln Cys Gly Leu Asn Asp Glu Thr
        195                 200                 205

Trp Tyr Ile Leu Ser Ser Cys Ile Gly Ser Phe Phe Ala Pro Cys Leu
    210                 215                 220
```

-continued

Ile Met Gly Leu Val Tyr Ala Arg Ile Tyr Arg Val Ala Lys Leu Arg
225 230 235 240

Thr Arg Thr Leu Ser Glu Lys Arg Ala Pro Val Gly Pro Asp Gly Ala
245 250 255

Ser Pro Thr Thr Glu Asn Gly Leu Gly Ala Ala Ala Gly Ala Gly Glu
260 265 270

Asn Gly His Cys Ala Pro Pro Pro Ala Asp Val Glu Pro Asp Glu Ser
275 280 285

Ser Ala Ala Ala Glu Arg Arg Arg Arg Arg Gly Ala Leu Arg Arg Gly
290 295 300

Gly Arg Arg Arg Ala Gly Ala Glu Gly Gly Ala Gly Gly Ala Asp Gly
305 310 315 320

Gln Gly Ala Gly Pro Gly Ala Ala Glu Ser Gly Ala Leu Thr Ala Ser
325 330 335

Arg Ser Pro Gly Pro Gly Gly Arg Leu Ser Arg Ala Ser Ser Arg Ser
340 345 350

Val Glu Phe Phe Leu Ser Arg Arg Arg Arg Ala Arg Ser Ser Val Cys
355 360 365

Arg Arg Lys Val Ala Gln Ala Arg Glu Lys Arg Phe Thr Phe Val Leu
370 375 380

Ala Val Val Met Gly Val Phe Val Leu Cys Trp Phe Pro Phe Phe Phe
385 390 395 400

Ser Tyr Ser Leu Tyr Gly Ile Cys Arg Glu Ala Cys Gln Val Pro Gly
405 410 415

Pro Leu Phe Lys Phe Phe Phe Trp Ile Gly Tyr Cys Asn Ser Ser Leu
420 425 430

Asn Pro Val Ile Tyr Thr Val Phe Asn Gln Asp Phe Arg Arg Ser Phe
435 440 445

Lys His Ile Leu Phe Arg Arg Arg Arg Arg Gly Phe Arg Gln
450 455 460

<210> SEQ ID NO 6
<211> LENGTH: 4
<212> TYPE: PRT
<213> ORGANISM: homo sapiens

<400> SEQUENCE: 6

Gly Ala Gly Pro
1

<210> SEQ ID NO 7
<211> LENGTH: 458
<212> TYPE: PRT
<213> ORGANISM: homo sapiens

<400> SEQUENCE: 7

Met Ala Ser Pro Ala Leu Ala Ala Ala Leu Ala Val Ala Ala Ala Ala
1 5 10 15

Gly Pro Asn Ala Ser Gly Ala Gly Glu Arg Gly Ser Gly Gly Val Ala
20 25 30

Asn Ala Ser Gly Ala Ser Trp Gly Pro Pro Arg Gly Gln Tyr Ser Ala
35 40 45

Gly Ala Val Ala Gly Leu Ala Ala Val Val Gly Phe Leu Ile Val Phe
50 55 60

Thr Val Val Gly Asn Val Leu Val Val Ile Ala Val Leu Thr Ser Arg
65 70 75 80

-continued

```
Ala Leu Arg Ala Pro Gln Asn Leu Phe Leu Val Ser Leu Ala Ser Ala
                85                  90                  95

Asp Ile Leu Val Ala Thr Leu Val Met Pro Phe Ser Leu Ala Asn Glu
            100                 105                 110

Leu Met Ala Tyr Trp Tyr Phe Gly Gln Val Trp Cys Gly Val Tyr Leu
        115                 120                 125

Ala Leu Asp Val Leu Phe Cys Thr Ser Ser Ile Val His Leu Cys Ala
    130                 135                 140

Ile Ser Leu Asp Arg Tyr Trp Ser Val Thr Gln Ala Val Glu Tyr Asn
145                 150                 155                 160

Leu Lys Arg Thr Pro Arg Arg Val Lys Ala Thr Ile Val Ala Val Trp
                165                 170                 175

Leu Ile Ser Ala Val Ile Ser Phe Pro Pro Leu Val Ser Leu Tyr Arg
            180                 185                 190

Gln Pro Asp Gly Ala Ala Tyr Pro Gln Cys Gly Leu Asn Asp Glu Thr
        195                 200                 205

Trp Tyr Ile Leu Ser Ser Cys Ile Gly Ser Phe Phe Ala Pro Cys Leu
    210                 215                 220

Ile Met Gly Leu Val Tyr Ala Arg Ile Tyr Arg Val Ala Lys Leu Arg
225                 230                 235                 240

Thr Arg Thr Leu Ser Glu Lys Arg Ala Pro Val Gly Pro Asp Gly Ala
                245                 250                 255

Ser Pro Thr Thr Glu Asn Gly Leu Gly Ala Ala Ala Gly Ala Gly Glu
            260                 265                 270

Asn Gly His Cys Ala Pro Pro Pro Ala Asp Val Glu Pro Asp Glu Ser
        275                 280                 285

Ser Ala Ala Ala Glu Arg Arg Arg Arg Arg Gly Ala Leu Arg Arg Gly
    290                 295                 300

Gly Arg Arg Arg Ala Gly Ala Glu Gly Gly Ala Gly Gly Ala Asp Gly
305                 310                 315                 320

Gln Gly Ala Ala Glu Ser Gly Ala Leu Thr Ala Ser Arg Ser Pro Gly
                325                 330                 335

Pro Gly Gly Arg Leu Ser Arg Ala Ser Ser Arg Ser Val Glu Phe Phe
            340                 345                 350

Leu Ser Arg Arg Arg Arg Ala Arg Ser Ser Val Cys Arg Arg Lys Val
        355                 360                 365

Ala Gln Ala Arg Glu Lys Arg Phe Thr Phe Val Leu Ala Val Val Met
    370                 375                 380

Gly Val Phe Val Leu Cys Trp Phe Pro Phe Phe Phe Ser Tyr Ser Leu
385                 390                 395                 400

Tyr Gly Ile Cys Arg Glu Ala Cys Gln Val Pro Gly Pro Leu Phe Lys
                405                 410                 415

Phe Phe Phe Trp Ile Gly Tyr Cys Asn Ser Ser Leu Asn Pro Val Ile
            420                 425                 430

Tyr Thr Val Phe Asn Gln Asp Phe Arg Arg Ser Phe Lys His Ile Leu
        435                 440                 445

Phe Arg Arg Arg Arg Arg Gly Phe Arg Gln
    450                 455
```

<210> SEQ ID NO 8
<211> LENGTH: 4
<212> TYPE: PRT
<213> ORGANISM: homo sapiens

-continued

<400> SEQUENCE: 8

Gly Ala Ala Glu
1

<210> SEQ ID NO 9
<211> LENGTH: 1431
<212> TYPE: DNA
<213> ORGANISM: homo sapiens

<400> SEQUENCE: 9
atgggcgcgg gggtgctcgt cctgggcgcc tccgagcccg gtaacctgtc gtcggccgca 60
ccgctccccg acggcgcggc caccgcggcg cggctgctgg tgcccgcgtc gccgcccgcc 120
tcgttgctgc ctcccgccag cgaaagcccc gagccgctgt ctcagcagtg gacagcgggc 180
atgggtctgc tgatggcgct catcgtgctg ctcatcgtgg cgggcaatgt gctggtgatc 240
gtggccatcg ccaagacgcc gcggctgcag acgctcacca acctcttcat catgtccctg 300
gccagcgccg acctggtcat ggggctgctg gtggtgccgt tcggggccac catcgtggtg 360
tggggccgct gggagtacgg ctccttcttc tgcgagctgt ggacctcagt ggacgtgctg 420
tgcgtgacgg ccagcatcga gaccctgtgt gtcattgccc tggaccgcta cctcgccatc 480
acctcgccct tccgctacca gagcctgctg acgcgcgcgc gggcgcgggg cctcgtgtgc 540
accgtgtggg ccatctcggc cctggtgtcc ttcctgccca tcctcatgca ctggtggcgg 600
gcggagagcg acgaggcgcg ccgctgctac aacgacccca agtgctgcga cttcgtcacc 660
aaccgggcct acgccatcgc ctcgtccgta gtctccttct acgtgcccct gtgcatcatg 720
gccttcgtgt acctgcgggt gttccgcgag gcccagaagc aggtgaagaa gatcgacagc 780
tgcgagcgcc gtttcctcgg cggcccagcg cggccgccct cgccctcgcc ctcgcccgtc 840
cccgcgcccg cgccgccgcc cggacccccg cgcccgccg ccgccgccgc caccgccccg 900
ctggccaacg ggcgtgcggg taagcggcgg ccctcgcgcc tcgtggccct acgcgagcag 960
aaggcgctca agacgctggg catcatcatg ggcgtcttca cgctctgctg gctgcccttc 1020
ttcctggcca acgtggtgaa ggccttccac cgcgagctgg tgcccgaccg cctcttcgtc 1080
ttcttcaact ggctgggcta cgccaactcg gccttcaacc ccatcatcta ctgccgcagc 1140
cccgacttcc gcaaggcctt ccagggactg ctctgctgcg cgcgcagggc tgcccgccgg 1200
cgccacgcga cccacggaga ccggccgcgc gcctcgggct gtctggcccg gcccggaccc 1260
ccgccatcgc ccggggccgc ctcggacgac gacgacgacg atgtcgtcgg ggccacgccg 1320
cccgcgcgcc tgctggagcc ctgggccggc tgcaacggcg gggcggcggc ggacagcgac 1380
tcgagcctgg acgagccgtg ccgccccggc ttcgcctcgg aatccaaggt g 1431

<210> SEQ ID NO 10
<211> LENGTH: 477
<212> TYPE: PRT
<213> ORGANISM: homo sapiens

<400> SEQUENCE: 10

Met Gly Ala Gly Val Leu Val Leu Gly Ala Ser Glu Pro Gly Asn Leu
1 5 10 15

Ser Ser Ala Ala Pro Leu Pro Asp Gly Ala Ala Thr Ala Ala Arg Leu
20 25 30

Leu Val Pro Ala Ser Pro Pro Ala Ser Leu Leu Pro Pro Ala Ser Glu
35 40 45

Ser Pro Glu Pro Leu Ser Gln Gln Trp Thr Ala Gly Met Gly Leu Leu

-continued

```
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475
```

-continued

<210> SEQ ID NO 11
<211> LENGTH: 1431
<212> TYPE: DNA
<213> ORGANISM: homo sapiens

<400> SEQUENCE: 11
atgggcgcgg gggtgctcgt cctgggcgcc tccgagcccg gtaacctgtc gtcggccgca 60
ccgctccccg acggcgcggc caccgcggcg cggctgctgg tgcccgcgtc gccgcccgcc 120
tcgttgctgc ctcccgccag cgaaagcccc gagccgctgt ctcagcagtg gacagcgggc 180
atgggtctgc tgatggcgct catcgtgctg ctcatcgtgg cgggcaatgt gctggtgatc 240
gtggccatcg ccaagacgcc gcggctgcag acgctcacca acctcttcat catgtccctg 300
gccagcgccg acctggtcat ggggctgctg gtggtgccgt tcggggccac catcgtggtg 360
tggggccgct gggagtacgg ctccttcttc tgcgagctgt ggacctcagt ggacgtgctg 420
tgcgtgacgg ccagcatcga gaccctgtgt gtcattgccc tggaccgcta cctcgccatc 480
acctcgccct tccgctacca gagcctgctg acgcgcgcgc gggcgcgggg cctcgtgtgc 540
accgtgtggg ccatctcggc cctggtgtcc ttcctgccca tcctcatgca ctggtggcgg 600
gcggagagcg acgaggcgcg ccgctgctac aacgacccca agtgctgcga cttcgtcacc 660
aaccgggcct acgccatcgc ctcgtccgta gtctccttct acgtgcccct gtgcatcatg 720
gccttcgtgt acctgcgggt gttccgcgag gcccagaagc aggtgaagaa gatcgacagc 780
tgcgagcgcc gtttcctcgg cggcccagcg cggccgccct cgccctcgcc ctcgcccgtc 840
cccgcgcccg cgccgccgcc cggacccccg cgccccgccg ccgccgccgc caccgccccg 900
ctggccaacg ggcgtgcggg taagcggcgg ccctcgcgcc tcgtggccct acgcgagcag 960
aaggcgctca agacgctggg catcatcatg ggcgtcttca cgctctgctg gctgcccttc 1020
ttcctggcca acgtggtgaa ggccttccac cgcgagctgg tgcccgaccg cctcttcgtc 1080
ttcttcaact ggctgggcta cgccaactcg gccttcaacc ccatcatcta ctgccgcagc 1140
cccgacttcc gcaaggcctt ccagcgactg ctctgctgcg cgcgcagggc tgcccgccgg 1200
cgccacgcga cccacggaga ccggccgcgc gcctcgggct gtctggcccg gcccggaccc 1260
ccgccatcgc ccggggccgc ctcggacgac gacgacgacg atgtcgtcgg ggccacgccg 1320
cccgcgcgcc tgctggagcc ctgggccggc tgcaacggcg gggcggcggc ggacagcgac 1380
tcgagcctgg acgagccgtg ccgccccggc ttcgcctcgg aatccaaggt g 1431

<210> SEQ ID NO 12
<211> LENGTH: 477
<212> TYPE: PRT
<213> ORGANISM: homo sapiens

<400> SEQUENCE: 12

Met Gly Ala Gly Val Leu Val Leu Gly Ala Ser Glu Pro Gly Asn Leu
1 5 10 15

Ser Ser Ala Ala Pro Leu Pro Asp Gly Ala Ala Thr Ala Ala Arg Leu
20 25 30

Leu Val Pro Ala Ser Pro Pro Ala Ser Leu Leu Pro Pro Ala Ser Glu
35 40 45

Ser Pro Glu Pro Leu Ser Gln Gln Trp Thr Ala Gly Met Gly Leu Leu
50 55 60

Met Ala Leu Ile Val Leu Leu Ile Val Ala Gly Asn Val Leu Val Ile
65 70 75 80

-continued

```
Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Arg Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475
```

<210> SEQ ID NO 13
<211> LENGTH: 29

-continued

```
<212> TYPE: DNA
<213> ORGANISM: homo sapiens

<400> SEQUENCE: 13

acgggcaggg ggcggggccg ggggcggct                                   29


<210> SEQ ID NO 14
<211> LENGTH: 17
<212> TYPE: DNA
<213> ORGANISM: homo sapiens

<400> SEQUENCE: 14

acgggcaggg ggcggct                                                17


<210> SEQ ID NO 15
<211> LENGTH: 19
<212> TYPE: DNA
<213> ORGANISM: homo sapiens

<400> SEQUENCE: 15

gccttccagg gactgctct                                              19


<210> SEQ ID NO 16
<211> LENGTH: 19
<212> TYPE: DNA
<213> ORGANISM: homo sapiens

<400> SEQUENCE: 16

gccttccagc gactgctct                                              19
```